US009144667B2

(12) United States Patent
Dolan

(10) Patent No.: US 9,144,667 B2
(45) Date of Patent: Sep. 29, 2015

(54) PROSTHETIC VALVE DELIVERY SYSTEM

(75) Inventor: Mark Dolan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 354 days.

(21) Appl. No.: 13/585,210

(22) Filed: Aug. 14, 2012

(65) Prior Publication Data
US 2012/0310334 A1 Dec. 6, 2012

Related U.S. Application Data

(60) Continuation of application No. 13/210,675, filed on Aug. 16, 2011, now Pat. No. 8,273,120, which is a division of application No. 12/403,114, filed on Mar. 12, 2009, now Pat. No. 8,021,420.

(51) Int. Cl.
| | |
|---|---|
| *A61F 2/24* | (2006.01) |
| *A61M 25/10* | (2013.01) |
| *A61M 29/02* | (2006.01) |
| *A61M 25/00* | (2006.01) |

(52) U.S. Cl.
CPC .......... *A61M 25/1011* (2013.01); *A61F 2/2433* (2013.01); *A61F 2/2436* (2013.01); *A61M 29/02* (2013.01); *A61F 2/2418* (2013.01); *A61F 2250/0048* (2013.01); *A61M 2025/004* (2013.01); *A61M 2025/0039* (2013.01)

(58) Field of Classification Search
CPC . A61M 25/1011; A61M 29/02; A61F 2/2433; A61F 2/2436
USPC .............. 623/1.1–1.12, 1.15–2.19, 1.23, 900
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,133,732 A | 7/1992 | Wiktor | |
| 5,292,331 A | 3/1994 | Boneau | |
| 5,421,955 A | 6/1995 | Lau | |
| 5,634,928 A * | 6/1997 | Fischell et al. ............... | 623/1.11 |

(Continued)

OTHER PUBLICATIONS

Webb et al., "A New Transcatheter Aortic Valve and Percutaneous Valve Delivery System" Journal of the American College of Cardiology, vol. 53. No. 20, May 19, 2009.

(Continued)

*Primary Examiner* — Gregory Anderson
*Assistant Examiner* — Son Dang

(57) ABSTRACT

A prosthetic valve delivery system for percutaneously delivering and deploying a prosthetic valve within an existing valve is disclosed. The delivery system includes a stented prosthetic valve having a balloon-expandable stent portion with a prosthetic valve disposed therein and at least one self-expanding stent portion. The delivery system further includes a dual balloon catheter having a first balloon on which the stented prosthetic valve is disposed during delivery and a second balloon. Upon delivery within the existing valve, the self-expanding stent portion contacts the existing valve and the first balloon expands the balloon-expandable stent portion to a first diameter such that the stented prosthetic valve is in a first stage deployment configuration. The second balloon then expands the balloon-expandable stent portion to a second diameter, greater than the first diameter, such that the stented prosthetic valve is in a second stage deployment configuration being fully deployed within the existing valve.

12 Claims, 8 Drawing Sheets

(56) References Cited

U.S. PATENT DOCUMENTS

| | | | |
|---|---|---|---|
| 5,776,161 A | 7/1998 | Globerman | |
| 5,935,162 A | 8/1999 | Dang | |
| 5,957,949 A | 9/1999 | Leonhardt et al. | |
| 6,090,127 A | 7/2000 | Globerman | |
| 6,113,627 A | 9/2000 | Jang | |
| 6,156,053 A | 12/2000 | Gandhi et al. | |
| 6,221,043 B1 | 4/2001 | Fischell et al. | |
| 6,361,544 B1 | 3/2002 | Wilson et al. | |
| 6,425,916 B1 * | 7/2002 | Garrison et al. | 623/2.11 |
| 6,663,661 B2 | 12/2003 | Boneau | |
| 6,730,116 B1 | 5/2004 | Wolinsky et al. | |
| 7,018,408 B2 | 3/2006 | Bailey et al. | |
| 7,105,015 B2 | 9/2006 | Goshgarian | |
| 7,585,321 B2 * | 9/2009 | Cribier | 623/2.14 |
| 2002/0151970 A1 | 10/2002 | Garrison et al. | |
| 2003/0079752 A1 | 5/2003 | Hart et al. | |
| 2003/0105516 A1 | 6/2003 | Austin | |
| 2004/0093058 A1 * | 5/2004 | Cottone et al. | 623/1.11 |
| 2004/0111111 A1 | 6/2004 | Lin | |
| 2005/0154447 A1 | 7/2005 | Goshgarian | |
| 2005/0251251 A1 * | 11/2005 | Cribier | 623/2.11 |
| 2009/0192601 A1 * | 7/2009 | Rafiee et al. | 623/2.11 |
| 2009/0306755 A1 * | 12/2009 | Dickinson et al. | 623/1.3 |

OTHER PUBLICATIONS

Nietlispach et al., "Current Balloon-Expandable Transcatheter Heart Valve and Delivery Systems" Catheterization and Cardiovascular Interventions 75:295-300, Feb. 1, 2010.

* cited by examiner

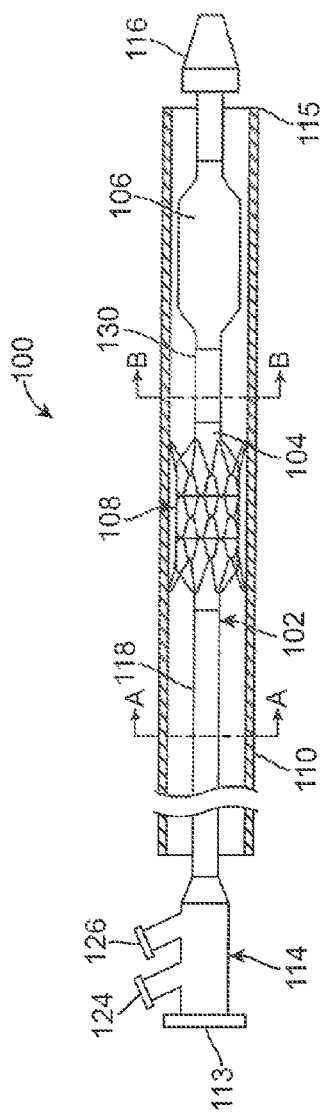

PROSTHETIC VALVE DELIVERY SYSTEM

RELATED APPLICATIONS

This application is a Continuation of and claims the benefit of U.S. patent application Ser. No. 13/210,675 filed Aug. 16, 2011, now Allowed; which is a Division of and claims the benefit of U.S. patent application Ser. No. 12/403,114 filed Mar. 12, 2009, now U.S. Pat. No. 8,021,420 issued Sep. 20, 2011. The disclosures of which are herein incorporated by reference in their entirety.

FIELD OF THE INVENTION

The invention relates generally to delivery systems for deploying a prosthetic heart valve in a non-coronary bypass procedure. More particularly, the invention relates to a catheter-based delivery system for deploying a prosthetic tissue valve having a stent framework with both balloon-expandable and self-expanding stent portions.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, such as those located within the arteries, veins gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One embodiment of a stented prosthetic valve is disclosed in U.S. Pat. No. 5,957,949 to Leonhardt et al. entitled "Percutaneous Placement Valve Stent", which is incorporated by reference herein in its entirety.

Due to the size of replacement heart valves, percutaneous delivery of a prosthetic heart valve necessitates a low profile delivery system in order to access the heart via the vasculature without performing a more invasive procedure. Some current delivery systems for delivering and deploying balloon-expandable prosthetic heart valves, for instance, are as large as 24 F, which is too large for femoral access in many patients, especially in female and pediatric subjects. Such delivery systems often include a large diameter balloon for expanding and deploying the balloon-expandable prosthetic heart valve, which undesirably adds significant bulk to the crossing profile of the delivery system.

When a prosthetic valve is deployed at the treatment site, a fundamental concern is that the prosthesis be deployed as precisely as possible, particularly where the prosthetic valve is used to replace an insufficient or incompetent heart valve. However, accurate positioning of the prosthetic valve may be difficult due to complexities in the anatomy as well as other factors, and an initial deployment of the prosthetic valve may result in a less than optimal positioning or, even worse, an inoperable positioning. As such it would be desirable that the prosthetic valve delivery system accommodate some re-positioning of the prosthetic valve prior to final deployment without adding to the crossing profile of the system.

Another concern when percutaneously delivering a prosthetic valve to replace a heart valve is whether deployment of the replacement heart valve can be accomplished without, or with minimal, blood stoppage during the interventional procedure. Minimizing or eliminating blood stoppage during an interventional procedure is desirable as it avoids complications associated with stopping the heart during the procedure.

Therefore, it would be desirable to have a low profile prosthetic valve delivery system that allows re-positioning of the prosthetic valve, if necessary, and that minimizes or eliminates blood flow stoppage during the valve replacement procedure.

BRIEF SUMMARY OF THE INVENTION

Embodiments hereof are directed to a low profile prosthetic valve delivery system for percutaneously delivering and deploying a prosthetic valve within a native or existing valve. The prosthetic valve delivery system includes a stented prosthetic valve having a balloon-expandable stent portion attached at an end to at least one self-expanding stent portion and having a prosthetic valve component disposed within and secured to the balloon-expandable stent portion. The prosthetic valve delivery system further includes a dual balloon catheter having a first balloon on which the stented prosthetic valve is disposed in a delivery configuration and a second balloon, wherein the first balloon has a first working diameter and the second balloon has a second working diameter that is greater than the first working diameter.

Upon delivery of the stented prosthetic valve within an existing valve, the self-expanding stent portion expands into contact with the existing valve and the first balloon expands the balloon-expandable stent portion to a first diameter such that the stented prosthetic valve is in a first stage deployment configuration. The second balloon is then manipulated to be disposed within the stented prosthetic valve in the first stage deployment configuration to expand the balloon-expandable stent portion to a second diameter greater than the first diameter such that the stented prosthetic valve is in a second stage deployment configuration. In the first stage deployment configuration an outer surface of the balloon-expandable stent portion is spaced from the existing valve, whereas in the second stage deployment configuration the outer surface of the balloon-expandable stent portion is in apposition with the existing valve. In an embodiment hereof, the first balloon is disposed on the dual balloon catheter proximal of the second balloon. In another embodiment hereof, the first balloon is disposed on the dual balloon catheter distal of the second balloon.

The prosthetic valve delivery system may further include an outer tubular sheath for radially constraining the self-expanding stent portion(s) of the stented prosthetic valve in the delivery configuration such that when the outer tubular sheath is proximally retracted relative to the self-expanding stent portion(s), the self-expanding stent portion(s) are released to deploy into an expanded configuration.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view in partial section of a prosthetic valve delivery system in a delivery configuration in accordance with an embodiment hereof.

FIG. 1A is a cross-sectional view of the prosthetic valve delivery system of FIG. 1 taken along line A-A.

FIG. 1B is a cross-sectional view of the prosthetic valve delivery system of FIG. 1 taken along line B-B.

DETAILED DESCRIPTION OF THE INVENTION

Figure 2:
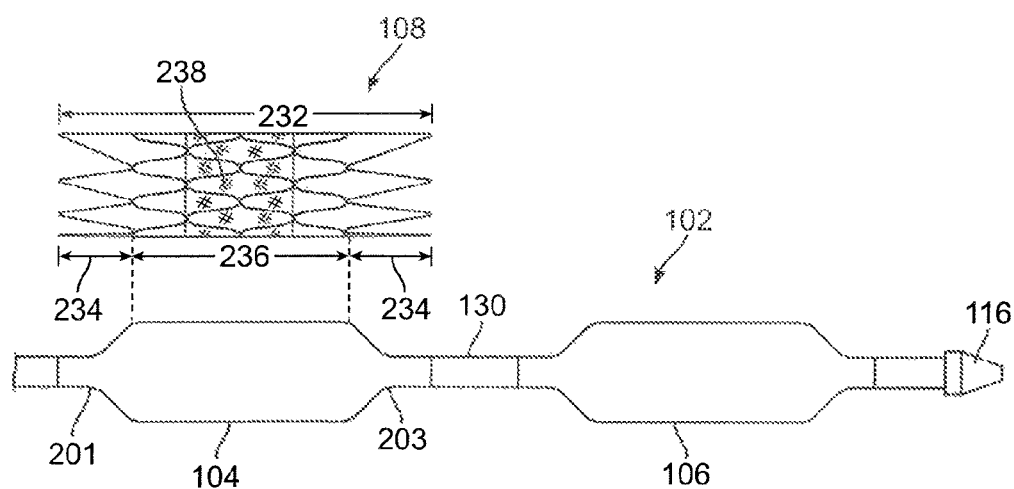
FIG. 2 is a side view of a distal portion of the prosthetic valve delivery system of FIG. 1 showing positioning of a stented prosthetic valve on a first balloon in the delivery configuration.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. However, when discussing positions of the delivery system and/or the prosthetic valve within the aorta proximate the heart, the terms "distal" and "proximal" are used in the following description with respect to the heart. More particularly, "distal" or "distally" are a position away from the heart and "proximal" or "proximally" are a position near or closer to the heart.

The following detailed description is merely exemplary in nature and is not intended to limit the invention or the application and uses of the invention. Although the description of the invention is in the context of heart valve replacement, the invention may also be used for valve replacement in other body passageways where it is deemed useful. Furthermore, there is no intention to be bound by any expressed or implied theory presented in the preceding technical field, background, brief summary or the following detailed description.

A prosthetic valve delivery system 100 in accordance with an embodiment hereof is shown and described with reference to FIGS. 1, 1A, and 1B. Prosthetic valve delivery system 100 includes a dual balloon catheter 102 having a first, proximal balloon 104 and a second, distal balloon 106, a stented prosthetic valve 108 mounted on proximal balloon 104 and an outer tubular sheath 110 slidably disposed over dual balloon catheter 102 and prosthetic valve 108.

Dual balloon catheter 102 includes a hub 114 positioned outside the patient and a soft distal tip 116 that aids in steering catheter 102 through the vasculature. Dual balloon catheter 102 has an over-the-wire catheter configuration with a guidewire lumen 112 for accommodating a guidewire (not shown) that extends from a proximal guidewire port 113 of hub 114 to distal tip 116. Guidewire lumen 112 has a proximal segment defined by a proximal shaft portion 118, which is coupled to hub 114 at a proximal end thereof and to proximal balloon 104 at a distal end thereof. As shown in cross-section in FIG. 1A, proximal shaft portion 118 is an extruded shaft that also defines a first inflation lumen 120 and a proximal segment of a second inflation lumen 122. First inflation lumen 120 extends between a first inflation fluid port 124 of hub 114 to an interior of proximal balloon 104, whereas second inflation lumen 122 extends between a second inflation fluid port 126 of hub 114 to an interior of distal balloon 106. As shown in cross-section in FIG. 1B, a distal segment of guidewire lumen 112 is defined by a guidewire shaft 128 that is concentrically disposed within a distal shaft portion 130, whereas a distal, annular segment of second inflation lumen 122 is defined between an exterior surface of guidewire shaft 128 and an interior surface of distal shaft portion 130. Each of distal shaft portion 130 and guidewire shaft 128 extends through proximal balloon 104 and is coupled to proximal shaft portion 110 such that each of guidewire lumen 112 and second inflation lumen 122 is a continuous lumen extending between hub 114 and distal tip 116 or distal balloon 106, respectively, as described above. A distal end of distal shaft portion 130 is coupled to distal balloon 106 and a distal portion of guidewire shaft 128 extends through distal balloon 106 to be coupled to distal tip 116. It would be understood by one of skill in the art of catheter construction that guidewire lumen 112, first inflation lumen 120, and second inflation lumen 122 may have alternate constructions and/or be of other shapes/sizes without departing from the scope of the present invention.

Outer tubular sheath 110, proximal shaft portion 118, distal shaft portion 130 and guidewire shaft 128 may be of any suitable flexible polymeric tubing used in catheter construction, such as tubing of polyethylene terephthalate (PET), polypropylene, nylon, polyethylene, polyether block amide (PEBA), fluoropolymers, such as polytetrafluoroethylene (PTFE), fluorinated ethylene propylene (FEP), or combinations thereof. Further as would be understood by one of ordinary skill in the art of catheter design, hub 114 provides a luer hub or other type of fitting that may be connected to sources of inflation fluid and may be of another construction or configuration without departing from the scope of the present invention.

Figure 3:
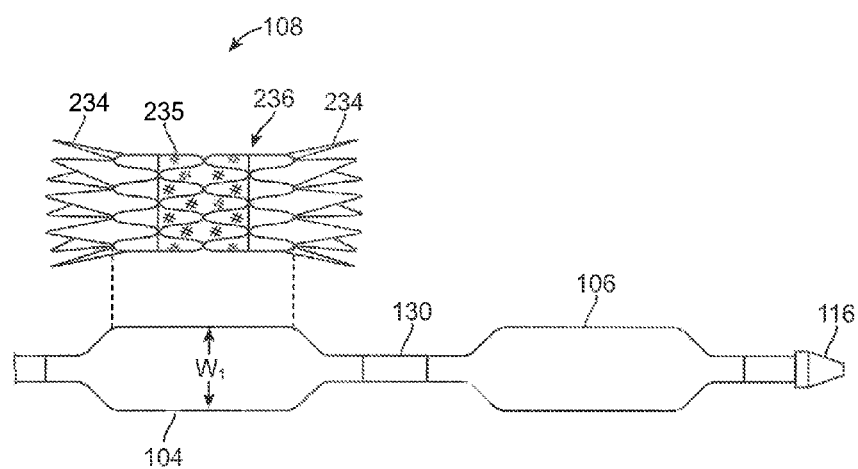
FIG. 3 is the distal portion of the prosthetic valve delivery system of FIG. 2 showing the stented prosthetic valve in a first stage deployment configuration with the first balloon expanded.
Figure 4:
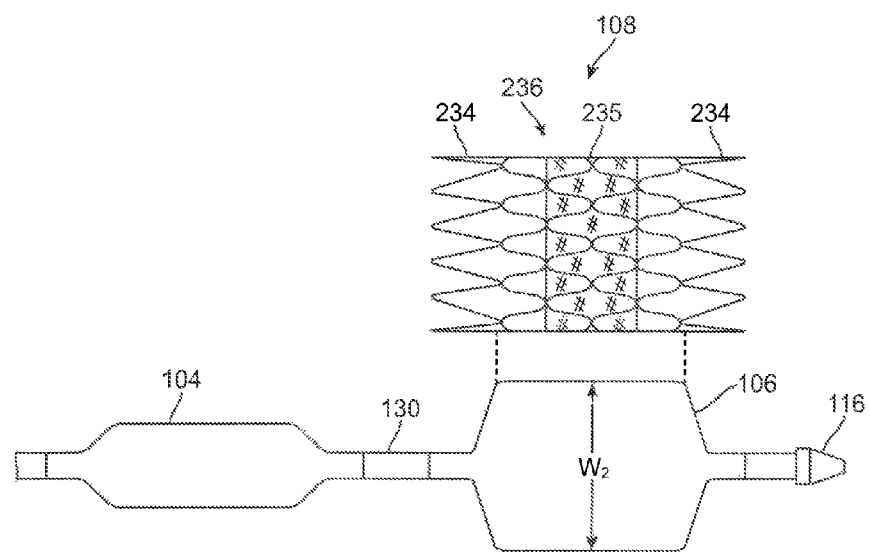
FIG. 4 is the distal portion of the prosthetic valve delivery system of FIG. 2 showing the stented prosthetic valve in a second stage deployment configuration with a second balloon expanded.

Proximal and distal balloons 104, 106 are dilatation balloons of a non-distensible, biocompatible material that may be expanded to a non-stretched working size or diameter upon the application of an inflation fluid at a given pressure. Suitable non-distensible biocompatible materials for fabricating proximal and distal balloons 104, 106 include but are not limited to nylon 12, nylon 10, polyester, and other polymer blends known in the art. As shown in FIGS. 3 and 4, proximal balloon 104 is formed to have a first working diameter $W_1$ and distal balloon 106 is formed to have a second working diameter $W_2$ that is greater than $W_1$ to effectuate a two-stage deployment of a balloon-expandable stent portion 236 of stented prosthetic valve 108, which will be described in greater detail below. By mounting balloon-expandable stent portion 236 of stented prosthetic valve 108 on the smaller proximal balloon 104 during delivery, as shown in FIG. 1, a crossing profile of the overall delivery system 100 may be reduced from a conventional delivery system that utilizes a single, larger diameter balloon for delivery and deployment. In another embodiment, first working diameter $W_1$ of proximal balloon 104 may be greater than second working diameter $W_2$ of distal balloon 106 such that balloon-expandable stent portion 236 of stented prosthetic valve 108 is mounted on distal balloon 106 during delivery.

Stented prosthetic valve 108 is constructed to prevent migration and paravalvular leakage when used in a replacement valve procedure. As best shown in FIGS. 2-4, stented prosthetic valve 108 includes a tubular stent assembly 232 having self-expanding stent portions 234 attached to respective proximal and distal ends of balloon-expandable stent portion 236, wherein a prosthetic valve 238 is disposed within and secured to balloon-expandable stent portion 236. When deployed in vivo, self-expanding stent portions 234 provide improved vessel compliance and sealing of stented prosthetic valve 108 while balloon-expandable stent portion 236 provides radial support for prosthetic valve 238. Self-expanding stent portions 234 may be attached to balloon-expandable stent portion 236 by sutures, welding or other attachment mechanism as would be known to one of ordinary skill in the art of stent construction. In an embodiment hereof where self-expanding stent portions 234 and balloon-expandable stent portion 236 are of dissimilar metals, a method of welding in accordance with U.S. Pat. Appl. Pub. No. 2005/0154447 to Goshgarian, which is incorporated by reference herein in its entirety, may be employed as the attachment mechanism. In another embodiment, a single self-expanding stent portion 234 may be attached to balloon-expandable stent portion 236 on a blood inflow end of stented prosthetic valve 108.

Prosthetic valve 238 includes valve leaflets that may be of a synthetic material, a xenograft natural tissue and/or a homograft natural tissue and may form a bicuspid, tricuspid, or tubular replacement valve. Synthetic materials suitable for use in embodiments hereof include DACRON® polyester (Invista North America S.A.R.L., Wilmington, Del., U.S.A.), nylon blends, and vacuum deposition nitinol fabricated materials. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Prosthetic valve 238 may be sutured or otherwise securely attached within balloon-expandable stent portion 236 of stent assembly 232 as would be known to one of ordinary skill in the art of prosthetic tissue valve construction.

Each self-expanding stent portion 234 is a tubular structure that includes a single sinusoidal ring attached at one or more peaks to balloon-expandable stent portion 236. Upon release of self-expanding stent portions 234 at a treatment site, self-expanding stent portions 234 are sized and constructed to expand into contact with a surface of the treatment site and to provide enough radial force to hold stented prosthetic valve 108 in place during the two-stage deployment of balloon-expandable stent portion 236, as discussed in detail below. In another embodiment, self-expanding stent portions 234 may each include more than one sinusoidal ring and means for securing the sinusoidal rings together. In another embodiment, self-expanding stent portions 234 may include an ePTFE or DACRON® covering. "Self-expanding" as used herein means that self-expanding stent portions 234 have a mechanical memory to return to an expanded or deployed configuration. Mechanical memory may be imparted to the wire or tubular structure that forms self-expanding stent portions 234 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. In embodiments hereof, self-expanding stent portions 234 may be made from stainless steel, a pseudo-elastic metal such as nitinol, or a so-called super alloy, which may have a base metal of nickel, cobalt, chromium, or other metal.

Balloon-expandable stent portion 236 is a tubular structure having four sinusoidal rings attached peak-to-peak and valley-to-valley. In another embodiment, balloon-expandable stent portion 236 may include fewer or more sinusoidal rings and have longitudinal connectors or other means for attaching the sinusoidal rings together. In various embodiments hereof, balloon-expandable stent portion 236 of stent assembly 232 may be constructed of, for e.g., platinum-iridium, cobalt chromium alloys (MP35N, L605), stainless steel, tantalum or other stent materials.

Some examples of self-expanding and balloon-expandable stents that may be adapted for use as stent portions 234, 236 in embodiments hereof are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,776,161 to Globerman, U.S. Pat. No. 5,935,162 to Dang, U.S. Pat. No. 6,090,127 to Globerman, U.S. Pat. No. 6,113,627 to Jang, U.S. Pat. No. 6,663,661 to Boneau, and U.S. Pat. No. 6,730,116 to Wolinsky et al., each of which is incorporated by reference herein in its entirety.

As illustrated in FIGS. 1 and 2, when balloon-expandable stent portion 236 with prosthetic valve 108 secured therein is crimped or otherwise collapsed onto proximal balloon 104 in the delivery configuration, self-expanding stent portions 234 extend over respective proximal and distal neck portions 201, 203 of proximal balloon 104 and are constrained in a contracted or compressed delivery configuration by outer tubular sheath 110. Once prosthetic valve delivery system 100 is tracked through the vasculature and positioned for treatment as discussed further below, outer tubular sheath 110 may be retracted to thereby release self-expanding stents 234 of stented valve prosthesis 108 so that they assume their expanded configuration (shown in FIG. 3) and contact a surface of the treatment site. An inflation fluid may then be introduced into proximal balloon 104 via first inflation fluid port 124 and first inflation lumen 120 to inflate proximal balloon 104 to working diameter $W_1$ and thereby expand balloon-expandable stent portion 236 to a first outer diameter in which stented valve prosthesis 108 is in an initial or first stage deployment configuration as shown in FIG. 3. Working diameter $W_1$ of proximal balloon 104 is sized to be less than a diameter of the body lumen in which stented prosthetic valve 108 is to be placed such that an exterior surface 235 of balloon-expandable stent portion 236 is spaced from the surface of the body lumen/treatment site to permit blood flow to continue during the first stage expansion of stented prosthetic valve 108. Proximal balloon 104 may then be deflated and proximally retracted leaving stented prosthetic valve 108 in its first stage deployment configuration to be held at the treatment site by the radial force provided by self-expanding stent portions 234. Distal balloon 106 may then be proximally retracted to be disposed within balloon-expandable stent portion 236 and an inflation fluid introduced into distal balloon 106 via second inflation fluid port 126 and second inflation lumen 122. Distal balloon 106 is then expanded to working diameter $W_2$ thereby radially expanding balloon-expandable stent portion 236 to a larger, second outer diameter in which stented valve prosthesis 108 is in a second stage deployment configuration as shown in FIG. 4, whereby prosthetic valve 238 is fully expanded. Working diameter $W_2$ of distal balloon 106 is sized to be approximately equal to a diameter of the body lumen in which stented valve 108 is to be placed such that exterior surface 235 of balloon-expandable stent portion 236 makes contact with the surface of the treatment site to be in apposition therewith.

The three phase deployment of stented prosthetic valve 108 permits a clinician to visualize under fluoroscopy the position of stented prosthetic valve 108 after deployment of self-expanding stent portions 234 and/or after first stage deployment of balloon-expandable stent portion 236. Such visualization may be used to confirm proper positioning of stented prosthetic valve 108 prior to second stage deployment of balloon-expandable stent portion 236, i.e., prior to full deployment of stented prosthetic valve 108. If improper positioning is identified, stented prosthetic valve 108 may be re-positioned by engagement with proximal balloon 104 at working diameter $W_1$. In an embodiment where stented prosthetic valve 108 is to be used to replace an incompetent aortic valve, such as described below with reference to FIGS. 5-8, visualizing the initial deployment positioning of the stented prosthetic valve can be used to assure that the coronary arteries will not blocked prior to final deployment of the stented prosthetic valve.

In another embodiment, dual balloon catheter 102 may be modified to include a single inflation lumen in fluid communication with both proximal and distal balloons 104, 106. Proximal balloon 104 may be constructed to fully expand to working diameter $W_1$ and distal balloon 106 may be constructed to fully expand to working diameter $W_2$, wherein in one embodiment $W_1$ is about half the size of $W_2$. During preliminary inflation of proximal balloon 104 with inflation fluid, distal balloon 106 does not substantially expand. After proximal balloon 104 has been used to expand stented prosthetic valve 108 into a first stage deployment configuration a vacuum may be pulled to deflate proximal balloon 104, as well as to remove any inflation fluid that may reside within distal balloon 106 so that distal balloon 106 may be proximally retracted and disposed within stented prosthetic valve 108. A second stage expansion of stented prosthetic valve 108 is then performed by introducing inflation fluid sufficient to expand distal balloon 106 and thereby expand stented prosthetic valve 108 into a second stage deployment configuration, i.e., full deployment. In another embodiment where dual balloon catheter 102 may be modified to include a single inflation lumen, proximal balloon 104 may be of a construction and a material that will fully expand to working diameter $W_1$ at 1 or 2 ATM, whereas distal balloon 106 may be of a construction and another material that will fully expand to working diameter $W_2$ at 3 ATM or greater.

In another embodiment, stent delivery system 100 may be modified to be of a rapid exchange (RX) catheter configuration without departing from the scope of the present invention such that guidewire lumen 112 only extends within a distal portion of catheter 102. In such an embodiment, proximal shaft portion 118 may include a metal hypotube with a guidewire transition area having a proximal guidewire port being positioned proximal of proximal balloon 104.

Figure 5:
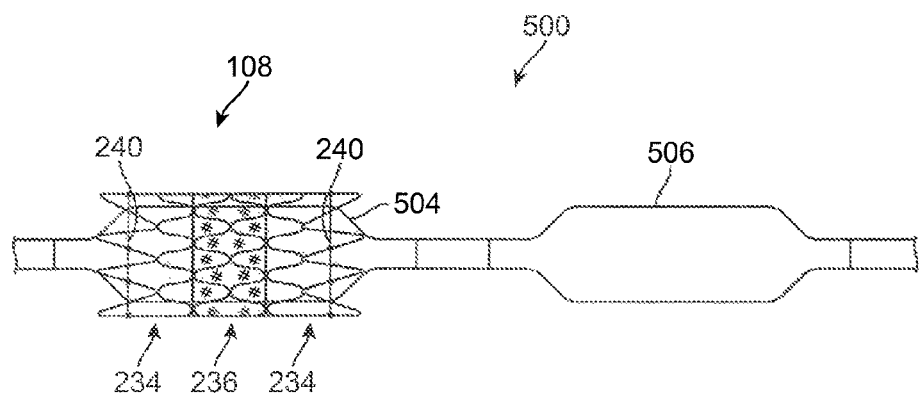
FIG. 5 is a side view of a distal portion of a prosthetic valve delivery system in accordance with another embodiment hereof showing positioning of a stented prosthetic valve on a first balloon in the delivery configuration.
Figure 5A:
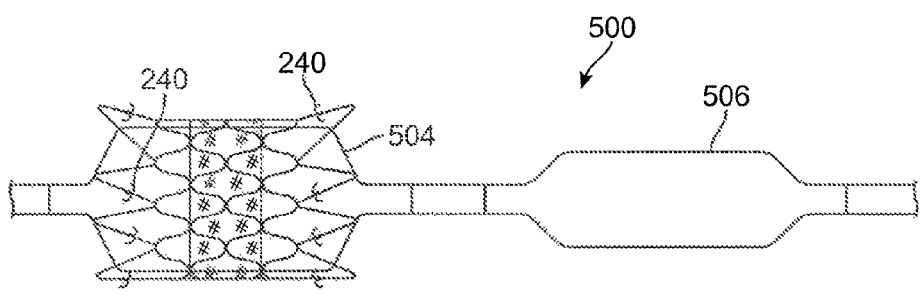
FIG. 5A is the distal portion of the prosthetic valve delivery system of FIG. 5 showing the stented prosthetic valve in a first stage deployment configuration with the first balloon expanded.

FIGS. 5 and 5A illustrate a side view of a distal portion of a prosthetic valve delivery system 500 having first and second balloons 504, 506 in accordance with another embodiment hereof. In contrast to prosthetic valve delivery system 100 which includes outer tubular sheath 110 for constraining self-expanding stent portions 234 of stented prosthetic valve 108 in a delivery configuration, prosthetic valve delivery system 500 utilizes frangible bands or ties 240 to constrain self-expanding stent portions 234 during delivery through the vasculature, as shown in FIG. 5. In such an embodiment, stented prosthetic valve 108 may be positioned on a longer, first balloon 504 of dual balloon catheter 502 with both balloon-expandable stent portion 236 and self-expanding stent portions 234 disposed around a working diameter $W_1$ of first balloon 504 during delivery and initial expansion. Frangible bands 240 temporarily hold self-expanding stent portions 234 in the collapsed, delivery configuration and are torn or broken upon or shortly after initial expansion of first balloon 504. As such, self-expanding stent portions 234 are released to expand into contact with the treatment site as first balloon 504 is expanded to its working diameter, which also expands balloon-expandable stent portion 236 to a first stage deployment configuration, as shown in FIG. 5A. Any feature and/or operation not described with reference to delivery system 500 can be considered similar or identical to those described with reference to delivery system 100.

Figure 6:
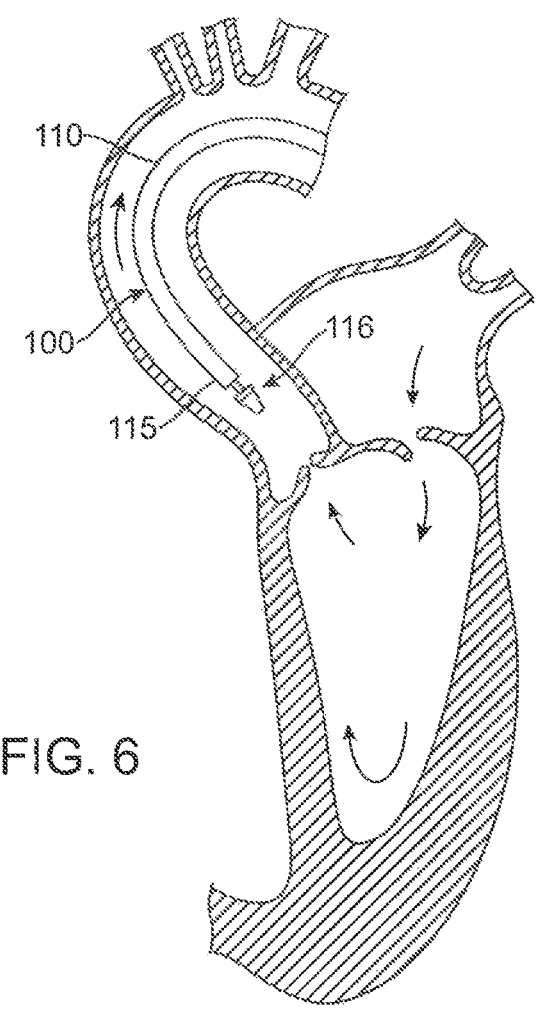
FIGS. 6-9 illustrate a method of using prosthetic valve delivery system 100 in a heart valve replacement procedure in accordance with an embodiment hereof.
Figure 7:
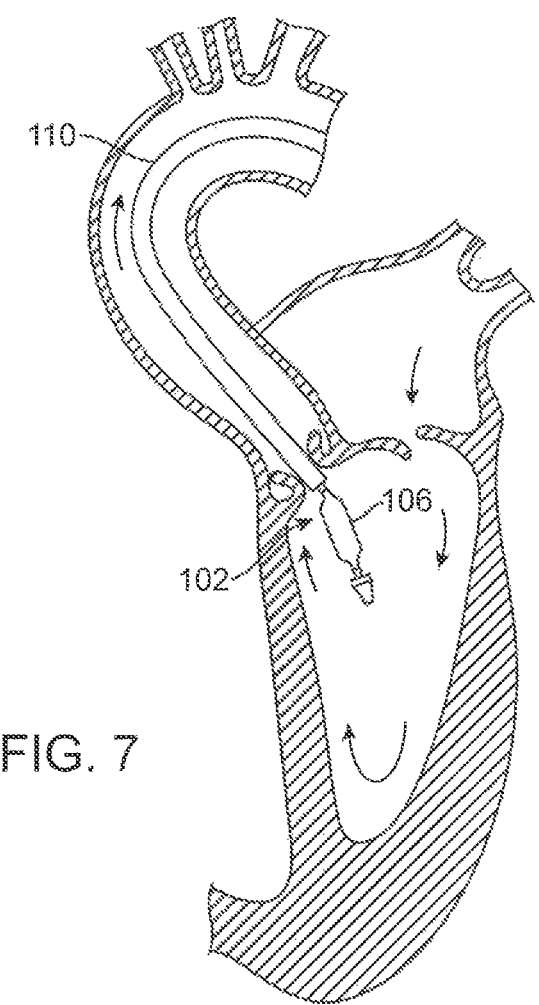
Figure 8:
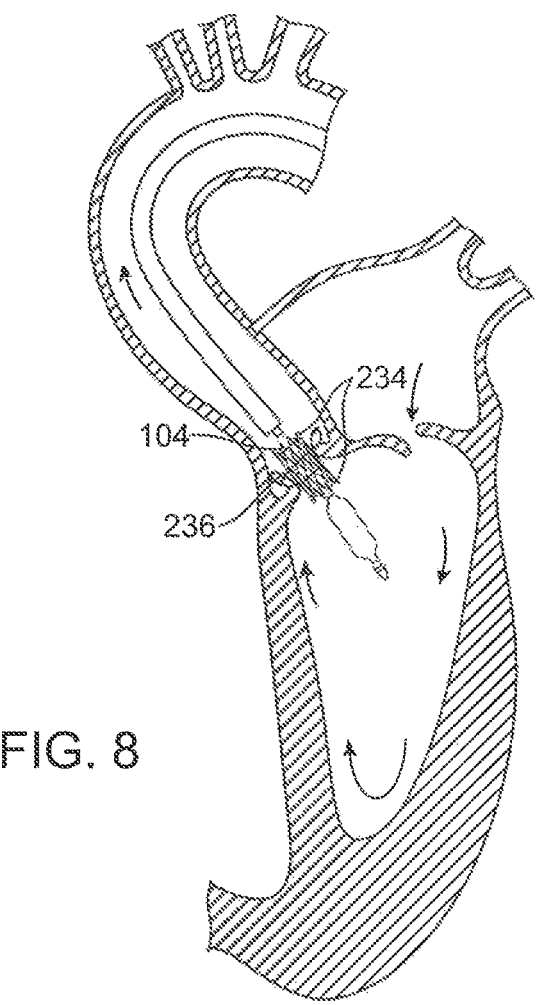

FIGS. 6-9 illustrate a method of using prosthetic valve delivery system 100 in accordance with an embodiment hereof to perform a heart valve replacement procedure, more particularly an aortic valve replacement, with minimal blood flow stoppage or interruption. Blood flow is represented by the arrows shown in each of the figures. With reference to FIG. 6, prosthetic valve delivery system 100 is shown after having been introduced into the vasculature via a percutaneous puncture, a.k.a the Seldinger technique, and having been tracked through the vasculature, over the aortic arch and into the descending aorta so that distal tip 116 is positioned proximate the aortic valve. Prosthetic valve delivery system 100 is then proximally advanced toward the heart until distal end 115 of outer tubular sheath 110 is positioned within the left ventricle such that delivery system 100 bridges the aortic valve with proximal balloon 104 and stented valve prosthesis 108 substantially concentrically positioned within the native aortic valve. Outer tubular sheath 110 is then retracted relative to dual balloon catheter 102, thereby leaving distal balloon 106 within the left ventricle, as shown in FIG. 7; however, blood flow is uninterrupted during this step of the method. Continued retraction of outer tubular sheath 110 releases self-expanding stent portions 234 of stented valve prosthesis 108 so that they provide a radial force to displace the native aortic valve leaflets and hold a concentric position of stented valve prosthesis 108 within the aortic root. Proximal balloon 104 may then be expanded to first working diameter $W_1$ to expand balloon-expandable portion 236 into the first stage deployment configuration shown in FIG. 8, wherein an outer surface of balloon-expandable stent portion 236 does not contact the native aortic valve. Further since first working diameter $W_1$ is sized to be less than the diameter of the native aortic valve, expansion of proximal balloon 104 to first working diameter $W_1$ does not block blood flow through the aortic valve, viz., the heart, during this step of the procedure. In an embodiment, first working diameter $W_1$ is sized to expand balloon-expandable stent portion 236 only enough to detach the balloon-expandable stent portion from proximal balloon 104. A preliminary position of stented prosthetic valve 108 may be checked via fluoroscopy to determine whether any re-positioning of the prosthetic valve is needed prior to deflating proximal balloon 104. If re-positioning is needed, stented prosthetic valve 108 is held in place only by self-expanding stent portions 234 with balloon-expandable stent portion 236 still attached to dual balloon catheter 102, i.e., in contact with inflated proximal balloon 104, such that adjustments to the position of stented prosthetic valve 108 can be made by pulling or pushing catheter 102.

Figure 9:
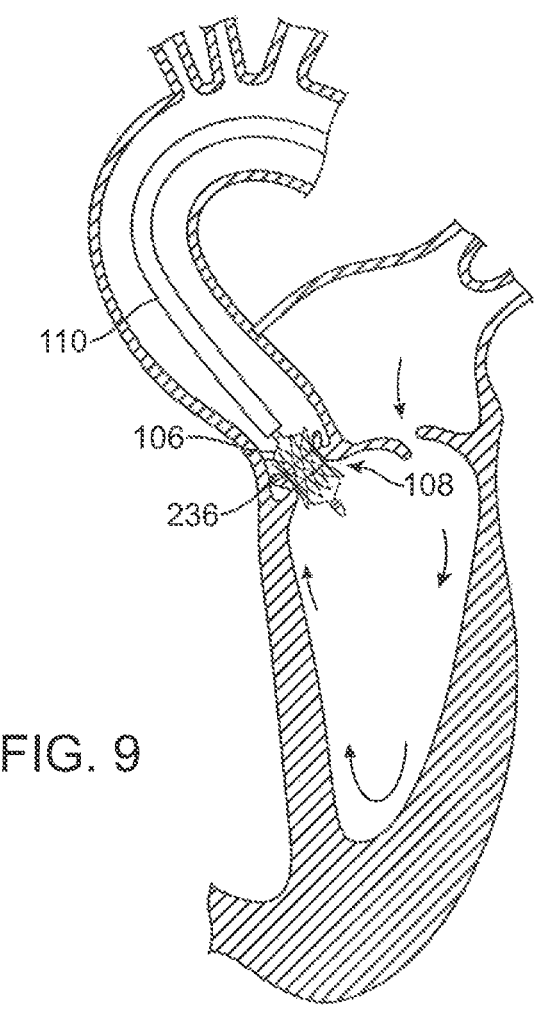

Once proximal balloon 104 is deflated, dual balloon catheter 102 is retracted within outer tubular sheath 110 until distal balloon 106 is concentrically disposed within stented prosthetic valve 108, and, more particularly, positioned within balloon-expandable stent portion 236. Distal balloon 106 may then be expanded to second working diameter $W_2$ to expand balloon-expandable portion 236 into the second or final stage deployment configuration shown in FIG. 9, wherein the outer surface of balloon-expandable stent portion 236 contacts the native aortic valve to be in apposition therewith. In some instances, during the step of positioning the second or distal balloon 106 within stented prosthetic valve 108, self-expanding stent portions 234 may not be sufficient to hold the prosthesis in position within the aortic valve with the heart beating normally, such that rapid pacing of the ventricles, i.e., inducing ventricle hyperactivity, may be necessary to inhibit the flow of blood through stented prosthetic valve 108 until distal balloon 108 has been inflated therein. In other instances, stopping blood flow may be necessary if the process of inflating the second or distal balloon 106 causes the pressure on the adjacent mitral valve to become too high. In this case, it may become necessary to again inhibit the function of the left ventricle by rapidly pacing the heart to prevent contractile displacement of the ventricle chamber. Distal balloon 106 is then deflated and prosthetic valve delivery system 100 is removed from the vasculature leaving stented prosthetic valve 108 deployed within the native aortic valve. Stented prosthetic valve 108 is constructed to prevent migration of the prosthesis and to avoid paravalvular leakage when used in a heart valve replacement procedure. When deployed within the native aortic valve as shown in FIG. 9, self-expanding stent portions 234 of stented prosthetic valve 108 provide improved compliance and sealing against the displaced aortic valve leaflets and/or the aortic root while balloon-expandable stent portion 236 provides radial support for prosthetic valve 238.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A prosthetic valve delivery system comprising:
   a stented prosthetic valve having a tubular stent assembly and a prosthetic valve component for deployment within a native valve, wherein the tubular stent assembly comprises a self-expanding portion and a balloon-expandable portion, and wherein the prosthetic valve component is disposed within and secured to the balloon-expandable stent portion of the tubular stent assembly;
   a delivery catheter having a first valve delivery location about which the entire stented prosthetic valve is disposed in a delivery configuration, and a second valve delivery location, located distally from the first valve delivery location, having a balloon for expanding the balloon-expandable portion of the stented prosthetic valve, wherein no portion of the stented prosthetic valve is disposed on the balloon of the second valve delivery location in the delivery configuration, and
   an outer sheath slidably disposed about the first and second valve delivery locations of the delivery catheter, wherein the outer sheath radially constrains the self-expanding portion of the stented prosthetic valve in the delivery configuration at the first valve delivery location and wherein retraction of the outer sheath proximal of the first valve delivery location deploys the self-expanding portion of the stented prosthetic valve into an expanded configuration with the balloon-expandable portion of the stented prosthetic valve remaining in the delivery configuration on the first valve delivery location,
   wherein the first valve delivery location has a first diameter and the second valve delivery location has a second diameter, wherein the second diameter is greater than or equal to the first diameter, and
   wherein the second diameter can be expanded by inflation of the balloon.

2. The delivery system of claim 1, wherein disposing the stented prosthetic valve about the first valve delivery location prior to the second valve delivery location reduces an overall diameter of the delivery system.

3. The delivery system of claim 1, wherein the first diameter is less than a diameter of a body lumen where the stented prosthetic valve is to be implanted, and the second diameter can be expanded to a diameter approximately equal to the body lumen where the stented prosthetic valve is to be implanted.

4. The delivery system of claim 1, wherein the delivery system can be manipulated to dispose the stented prosthetic valve about the second delivery location after being disposed about the first delivery location.

5. The delivery system of claim 1, wherein the balloon-expandable portion of the stented prosthetic valve is crimped about the first valve delivery location.

6. The delivery system of claim 1, wherein the delivery catheter further comprises a distal tip, wherein the distal tip is tapered from a proximal end to a distal end.

7. The delivery system of claim 1, wherein the delivery catheter is a flexible, steerable delivery catheter.

8. The delivery system of claim 1, wherein the delivery catheter further comprises a guide wire lumen.

9. The delivery system of claim 8, further comprising a guide wire.

10. A prosthetic valve delivery system comprising:
a stented prosthetic valve having a tubular stent assembly and a prosthetic valve component for deployment within a native valve,
wherein a self-expanding portion of the tubular stent assembly is configured to contact native valve leaflets and to provide a radial force to displace the native valve leaflets to hold the stented prosthetic valve in a deployment location;
a delivery catheter having a proximal valve delivery location with a proximal balloon about which the entire stented prosthetic valve is disposed in a collapsed delivery configuration, and a distal valve delivery location, located distally from the proximal valve delivery location, having a distal balloon for expanding the stented prosthetic valve, wherein no portion of the stented prosthetic valve is disposed on the distal balloon of the distal valve delivery location in the collapsed delivery configuration, and
an outer sheath slidably disposed about the proximal and distal valve delivery locations of the delivery catheter, wherein the outer sheath radially constrains the self-expanding portion of the stented prosthetic valve in the collapsed delivery configuration at the proximal valve delivery location, and wherein retraction of the outer sheath proximal of the proximal valve delivery location deploys the self-expanding portion of the stented prosthetic valve into an expanded configuration while a remaining portion of the stented prosthetic valve remains in the collapsed delivery configuration on the proximal balloon of the proximal valve delivery location, and
wherein the proximal balloon of the proximal valve delivery location has a first diameter and the distal balloon of the distal valve delivery location has a second diameter, wherein the second diameter is greater than or equal to the first diameter.

11. The delivery system of claim 10, wherein the remaining portion of the stented prosthetic valve includes a balloon-expandable stent portion of the tubular stent assembly.

12. The delivery system of claim 11, wherein the prosthetic valve component is disposed within and secured to the balloon-expandable stent portion of the stent assembly.

* * * * *